United States Patent [19]

Richter et al.

[11] 4,400,560

[45] Aug. 23, 1983

[54] PROCESS FOR THE PREPARATION OF A MIXTURE OF LOW-MOLECULAR WEIGHT POLYHORIC ALCOHOLS

[75] Inventors: Roland Richter, Leverkusen; Hanns P. Müller, Odenthal; Kuno Wagner, Leverkusen; Rudolf Helm, Bergisch Gladbach; Jürgen Zander, Leverkusen, all of Fed. Rep. of Germany

[73] Assignee: Bayer Aktiengesellschaft, Leverkusen, Fed. Rep. of Germany

[21] Appl. No.: 242,076

[22] Filed: Mar. 9, 1981

[30] Foreign Application Priority Data

Mar. 14, 1980 [DE] Fed. Rep. of Germany ....... 3009847

[51] Int. Cl.³ ............................................ C07C 31/18
[52] U.S. Cl. .................................. 568/863; 521/158; 528/275; 568/678; 568/679; 568/680
[58] Field of Search ........................................ 568/863

[56] References Cited

U.S. PATENT DOCUMENTS

| | | | |
|---|---|---|---|
| 2,174,651 | 10/1939 | Byrkit, Jr. ........................... | 568/863 |
| 2,271,083 | 1/1942 | Lorand ................................ | 260/635 |
| 2,276,192 | 3/1942 | Handford et al. .................. | 260/635 |
| 2,775,621 | 12/1956 | MacLean et al. .................. | 260/635 |
| 4,156,636 | 5/1979 | Muller et al. ....................... | 568/863 |
| 4,219,508 | 8/1980 | Wagner .............................. | 568/387 |
| 4,258,222 | 3/1981 | Mohring et al. .................... | 568/863 |
| 4,300,003 | 11/1981 | Mohring et al. .................... | 568/863 |

FOREIGN PATENT DOCUMENTS 988040 3/1965 United Kingdom ................ 568/863
1542980 3/1979 United Kingdom .

OTHER PUBLICATIONS

R. D. Partridge, A. H. Weiss & D. Todd, Carbohydrate Research, 24, 42 (1972).
L. Orthner and E. Gerisch (Biochem. Zeitung 259, 30 (1933).
Practical Catalytic Hydrogenation, Techniques & Applications, pp. 23-25, Wiley-Interscience, M. Friefelder (1971).

*Primary Examiner*—J. E. Evans
*Attorney, Agent, or Firm*—Gene Harsh; Joseph C. Gil; Lyndanne M. Whalen

[57] ABSTRACT

A process for preparing a mixture of polyhydroxyl compounds having low molecular weight by catalytically hydrogenating a formose mixture with hydrogen on a metal catalyst. The hydrogenation is carried out at a pH of 7.5 to 12.5 and at elevated temperature and pressure. The formose mixture comprises (i) up to 70 wt. % formose, (ii) up to 1.6 wt. % lead ions and (iii) up to 5 wt. % calcium ions with at least one of (ii) or (iii) being present. The catalyst which is present in an amount of 4-240 wt. % (based on formose solution) is a compound taken from the group consisting of nickel, cobalt and compounds thereof. The mixture of polyhydroxyl compounds made in accordance with the present invention is useful as a starting material in the production of polyether polyols, polyester polyols and polyurethane plastics.

11 Claims, No Drawings

PROCESS FOR THE PREPARATION OF A MIXTURE OF LOW-MOLECULAR WEIGHT POLYHORIC ALCOHOLS

BACKGROUND OF THE INVENTION

The present invention relates to a process for the preparation of a mixture of low-molecular weight polyhydric alcohols by the catalytic hydrogenation of formose. Formose is a mixture of low-molecular weight hydroxyaldehydes, hydroxyketones and polyhydric alcohols which is formed in the condensation of formaldehyde.

Since the work of Butlerow and Loew (Ann. 120, 295 (1861) and J. prakt. Chem. 33, 321 (1886)) hydroxyaldehydes and hydroxyketones have been formed by condensation of formaldehyde hydrate (formose synthesis). Formose has also been prepared by condensation of formaldehyde in the presence of lead-II compounds and of compounds capable of enediol formation, at a temperature of 70°-110° C. In this type of condensation, control of the pH of the reaction mixture is considered to be essential. Such pH control was generally achieved by the addition of an inorganic or organic base (see, e.g., German Offenlegungsschrift No. 2,639,084). In addition to formaldehyde, formose may also be prepared from mixtures of low-molecular hydroxyaldehydes and/or hydroxyketones and, if appropriate, polyhydric alcohols.

Many attempts have been made to convert mixtures of hydroxyaldehydes, hydroxyketones and/or polyalcohols into color-stable mixtures of polyalcohols. (Such polyol mixtures obtained by reduction of formoses are hereinafter called "formitols.") Sodium amalgam was used in the earliest processes (Loew, J. prakt. Chem. 33, 325 (1886)), but sodium borohydride has been used in more recent processes (compare R. D. Partridge, A. H. Weiss and D. Todd, Carbohydrate Research, 24, 42 (1972)). The reduction may also be accomplished electrochemically.

Process for the catalytic hydrogenation of sugars have also been modified in an effort to develop a process for producing a stable polyol mixture by the reduction of formose. The reaction conditions employed in each of these processes are quite different from those of the other processes particularly with respect to the nature and amount of catalyst and the concentration of the formose employed. For example, L. Orthner and E. Gerisch (Biochem. Zeitung 259, 30 (1933)) describe a process for the catalytic hydrogenation of formose in which a 4% strength aqueous formose solution is hydrogenated with 170% by weight (relative to formose) of Raney nickel for a period of 7-8 hours at 130° C. and under a hydrogen pressure of 120 bars. In some of the earlier processes which employed metal catalysts or noble metal catalysts (especially Raney nickel), hydrogenation in an alkaline medium was strictly avoided to prevent the occurrence of side reactions and discoloration (W. Langenbeck, J.f. prakt. Chemie 3, 206 (1956)).

None of these processes have, however, proven to be economically practicable. One possible explanation for this failure to develop an economical process for reducing formose by adaptation of known sugar processes is that due to the exceptional polymolecularity of formose, formose is substantially different from sugars.

Another reason that known formose-producing processes are uneconomical lies in the fact that basic inorganic salts such as Ca salts and Pb salts, are used as catalysts. These salts must be removed before the hydrogenation, especially the lead salts because lead is a powerful catalyst poison (see M. Freifelder, Practical Catalytic Hydrogenation, pages 24, 25, Wiley, New York (1971) and the literature quoted therein). Removal of these salts complicates the process and increases the cost. Methods for removing lead which have been developed include ion exchange (U.S. Pat. No. 2,775,621) and precipitation (U.S. Pat. Nos. 2,276,192 and 2,271,083) before the hydrogenation. In German Patent Specification No. 830,951 (page 1, lines 7-23), the troublesome calcium and lead ions are precipitated as carbonates to prevent undesired side reactions in the hydrogenation and poisoning of the Raney nickel catalyst. Complete deionization is not achieved in the latter procedure (though presumably almost all of the lead is removed) so the residual salt content is removed by ion exchange after the hydrogenation.

It would therefore be advantageous to develop a process for producing a mixture of polyhydroxyl compounds from formose which does not require the removal of the calcium and/or lead salt catalysts used in producing the formose.

SUMMARY OF THE INVENTION

It is an object of the present invention to provide a process for preparing a mixture of low-molecular weight polyhydroxyl compounds by catalytically hydrogenating a formose mixture.

It is also an object of the present invention to provide a process for catalytically hydrogenating a formose mixture in which lead ions and/or calcium ions are present.

It is a further object of the present invention to provide a process for making a colorless polyol mixture from formose.

These and other objects which will be apparent to those skilled in the art are accomplished by catalytically hydrogenating a formose mixture with hydrogen on a metal catalyst at a pH of 7.5 to 12.5 and at elevated temperature and pressure. The formose mixture comprises up to 70 wt. % formose and up to 1.6 wt. % lead ions and/or up to 5 wt. % calcium ions in which at least one of the group of lead ions or calcium ions must be present. The catalyst employed is a compound taken from the group consisting of nickel, cobalt and compounds thereof.

DETAILED DESCRIPTION OF THE INVENTION

A process has now been found for the preparation of a mixture of low-molecular polyhydroxy compounds from a formose mixture which contains lead and/or calcium ions. In this process, low-molecular weight hydroxyaldehydes, hydroxyketones and polyhydroxy compounds (i.e., formose) are catalytically hydrogenated with hydrogen on a metal catalyst under increased pressure and at elevated temperature. The pH of the reaction environment is maintained in the range of 7.5-12.5. The formose solution which is being hydrogenated contains up to 70% by weight of formose, has a content of lead ions of up to 1.6% by weight and/or of calcium ions of up to 5% by weight (based on the total weight of the formose solution). The formose solution may also contain ions of metals of Groups IA and/or IIA of the Periodic Table. Aldehydes and/or ketones and/or alcohols and/or sugars which do not originate from the preparation of the formose may also be added to the formose solution. The catalyst is a nickel or cobalt compound which may be present in the reaction environment in an amount of 4 to 240% by weight (based on 100% formose present in the hydrogenation reactor).

Mixtures of low-molecular hydroxyaldehydes, hydroxyketones and polyhydroxy compounds (i.e., formoses) which may be used in the process of the present invention may be prepared by techniques which are well known to those in the art. Several of these known processes are discussed in the Background of the Invention.

Solvents which may be used in making the formose solution used in the present invention include: water; a monoalcohol or polyalcohol, such as methanol, ethanol, propanol, butanol, isopropanol, isobutanol, cyclopentanol, cyclohexanol, 2-ethoxyethanol, 2-propoxyethanol, 2-isopropoxyethanol, 2-butoxyethanol, 2-(2-methoxyethoxy)-ethanol, 2-(2-ethoxyethoxy)-ethanol, 1,2-(bis-2-hydroxyethoxy)-ethane, ethylene glycol, diethylene glycol, triethylene glycol, tetraethylene glycol, 1,2-propanediol, isopropylene glycol, 1,3-propanediol, 1,2-butanediol, 1,3-butanediol, 1,4-butanediol, 2-methoxy-1-butanol, 2,3-butanediol, 1,5-pentanediol, 2.2-dimethyl-1,3-propanediol, 1,6-hexanediol, 2,5-hexanediol, 2-methyl-2,4-pentanediol, 3-methyl-1,5-pentanediol, 3-methyl-2,4-pentanediol, 2,3-dimethyl-2,3-butanediol, 2-methyl-2-propyl-1,3-propanediol, 2,2-diethyl-1,3-propanediol, 2-ethyl-1,3-hexanediol, 2,5-dimethyl-2,5-hexanediol, 2,2,4-trimethyl-1,3-pentanediol, 1,3-diethoxy-2-propanol, 2-hydroxymethyl-2-methyl-1,3-propanediol, 1,2,6-hexanetriol, 2-ethyl-2-hydroxymethyl-1,3-propanediol, 2,2-bis-hydroxymethyl-1,3-propanediol, erythritol, quinitol, mannitol, sorbitol and methylglycositol; ethoxylation and propoxylation products of these alcohols with a molecular weight of up to about 400; and mixtures of these alcohols. The preferred solvents are water, ethylene glycol, glycerol and 1,4-butanediol. Water is the particularly preferred solvent.

The concentration of formose in the formose solution may be up to 70% by weight (based on the total solution). The formose should be present in an amount in the range of 4 to 70% by weight, with 20-70% by weight being the preferred range and 35 to 70% by weight being the most preferred range.

The formose solution may also contain aldehydes and/or ketones and/or alcohols and/or sugars in an amount of up to 80% by weight (relative to the total amount of the products to be reduced), but preferably in an amount which is less than 30% by weight. Aldehydes which may be included in the formose solution used in the process of the present invention are acetaldehyde, propionaldehyde, butyraldehyde and isobutyraldehyde, and methylol derivatives thereof. Ketones which may be used are acetone, methyl ethyl ketone, diethyl ketone, cyclopentanone, cyclohexanone, mesityl oxide, isophorone, acetophenone and benzophenone and methylol derivatives thereof. Alcohols which may be used include the alcohols described above as suitable solvents and polyhydroxy compounds which (i) have a molecular weight of up to 10,000; (ii) are liquid or soluble in the formose solution at room temperature; and (iii) contain at least 2, as a rule 2 to 8, but preferably 2 to 4 hydroxyl groups. Examples of the latter type of polyhydroxy compound are polyesters, polyethers, polythioethers, polyacetals, polycarbonates and polyester-amides.

Sugars which may also be included in the formose solution used in the process according to the present invention are synthetic or natural sugars. Examples of these are: glucose; maltose; fructose; sucrose; lactose; synthetic invert sugars, such as hydrolysis products of sucrose; mixtures of sucrose and invert sugar; hydrolysis products of trehalose, maltose or isomaltose; hydrolysis products of maize starch and potato starch and pectic substances, such as amylose and amylopectins, cellobiose and lactose; hydrolysis and products of galactose; glucose mixtures; raffinose hydrolysis products; cellulose hydrolysis products; hydrolysis products of dextrins, optionally mixed with non-hydrolyzed dextrins; hydrolysis products of the Schardinger dextrins (cyclic dextrins); hydrolysis products of glycogen; hydrolysis products of glucose-6-phosphoric acid; hydrolysis products of glucose-1-phosphate (Cori ester); fructose-6-phosphate; degraded pectic substances (polygalacturonic acids); degraded glucosamines and hydrolysis products of molasses residues.

The aldehydes, ketones, alcohols and sugars mentioned above may be employed singly or as a mixture.

According to the present invention, a formose solution which has a content of lead ions of up to 1.6% by weight and/or of calcium ions of up to 5% by weight (relative to the total weight of the solution) is employed. Such formoses are formed, e.g., in the condensation of formaldehyde catalyzed by lead ions and/or calcium ions. A content of lead ions of from 1 to 16,000 ppm is within the acceptable range. The preferred lead ion content is from 20 to 2,000 ppm and the most preferred range is from 100 to 1,000 ppm. A content of calcium ions of 1 to 50,000 ppm is within the range described above as suitable. The preferred calcium ion concentration is from 100 to 40,000 ppm with the most preferred range being 1,000 to 30,000 ppm. It is also possible to hydrogenate formoses which have both calcium and lead present in amounts within the given ranges by the process of the present invention. Such a formose may be the result of mixed catalysis with lead ions and calcium ions. The amount of each of the two species of ions where both are present is considered independent of the other. Formoses which contain both lead ions and calcium ions are preferred in the process according to the present invention.

The presence of ions of other elements from Groups IA and IIA of the Periodic Table which may be present in the formose does not impair the mode of reaction of the process according to the present invention. Such ions are, for example, those of the elements sodium, potassium, lithium, magnesium, strontium and barium.

The process of the present invention must be carried out in the presence of a nickel or cobalt catalyst. Such a catalyst may be the pure element, a supported catalyst, alloy or mixture containing nickel and/or cobalt. Suitable elemental metal catalysts may be prepared by the direct reduction of nickel salts or cobalt salts or by reduction of nickel salts or cobalt salts with metal-alkyl compounds, alkali metal hydrides, hydrazine, borates or hydrogen boride, or by reduction of metal oxides or metal oxide, mixtures.

Supports which may be used for nickel-containing and/or cobalt-containing catalysts are both inorganic and organic materials. Suitable inorganic supports include: kieselguhr, silica, aluminum oxides, alkali metal silicates and alkaline earth metal silicates, aluminosilicates, montmorillonite, zeolites, spinels, dolomite, kaolin, magnesium silicates, zirconium oxide, zinc oxide, calcium carbonate, silicon carbide, aluminum phosphate, boron phosphate, asbestos and active charcoal. Appropriate organic materials which may be used as catalyst supports are naturally occurring or synthetic compounds of high molecular weight, such as silk, polyamides, polystyrenes, cellulose or polyurethanes. The support material may be in the form of balls, strands, filaments, cylinders or polygons, or in powder form.

Examples of nickel and/or cobalt catalysts which may be in the form of an alloy or mixture are catalysts of the Raney type, such as Raney nickel, Raney cobalt catalysts, Raney nickel/iron, Raney cobalt/nickel and Raney cobalt/iron. These catalysts may contain one or more of the following elements, as promoters, in amounts of up to 10% by weight of the catalyst weight: lithium, sodium, calcium, barium, potassium, silver, beryllium, lanthanum, cerium, vanadium, niobium, tantalum, molybdenum and tungsten. The above-mentioned catalysts may also contain one or more of the following elements in amounts of up to 1% by weight: ruthenium, rhodium, palladium, gold, iridium and platinum.

Nickel-containing catalysts, such as Raney nickel and Raney nickel/iron, which can optionally also contain calcium and/or sodium, are preferred in the process according to the present invention.

The catalyst should be employed in the process of the present invention in an amount of 4 to 240% by weight, calculated as the amount of active metal and based on 100% formose present in the hydrogenation reactor. The catalyst should preferably be used in an amount of 6 to 100% by weight, and most preferably 10 to 40% by weight (based on 100% formose).

The process according to the invention should be carried out at a pH between 7.5 and 12.5, preferably between 8.0 and 10.5. The pH value of the solution to be hydrogenated may be established with either inorganic or organic bases. Examples of suitable basic materials are sodium hydroxide, potassium hydroxide, calcium hydroxide, magnesium hydroxide, barium hydroxide, hydrated aluminum oxide, triethylamine, N-methylmorpholine and N-methylpiperidine. It is preferred that the base which had been used in the formose synthesis be used to adjust the pH of the hydrogenation mixture. For example, where calcium hydroxide had been employed both as a catalyst and as a pH regulator in the formose synthesis, it is particularly preferred that the pH value of the hydrogenation mixture used in the process according to the present invention be adjusted by means of calcium hydroxide.

The process according to the present invention should be carried out under a hydrogen pressure of 100 to 200 bars and at a temperature in the range from 80° to 200° C., preferably 100° to 180° C. and most preferably 130° to 180° C.

The process according to the present invention may be carried out on a continuous or non-continuous basis. Pressure reactors which are known to those in the art may be used. Such reactors may be provided with a stirring or mixing device. The catalyst may be in the form of a fixed bed or may be kept as a suspension in the formose to be hydrogenated. A suspended catalyst is preferred in a discontinuous process in a stirred or shaken reactor and in a continuous process carried out in a tube reactor.

The process according to the present invention may, for example, be carried out on a non-continuous basis in a pressure kettle provided with a stirring or mixing device. In such a procedure, the reactor should be approximately half-filled with a formitol (obtained by any of the processes known to those in the art) and at the same time charged with the catalyst. This mixture should then be subjected to preliminary hydrogenation at an appropriate hydrogenation temperature and pressure to activate the catalyst. The lead-containing and/or calcium-containing formose may then be introduced batch-wise into the reactor with the volume of each charge being about ⅛ to ¼ of the volume of the reactor. After pumping in a charge of formose, the mixture should be hydrogenated until the desired degree of hydrogenation is reached. An amount of the contents of the reactor corresponding to the amount of the formose charge pumped in may then be removed from the reactor, in a manner such that the catalyst remains in the reactor, before the next change is to be fed to the reactor. The catalyst should be present in the hydrogenation reactor in an amount of 4 to 240% by weight, preferably 10 to 100% by weight and most preferably 20 to 40% by weight (relative to the formose content of the individual charge pumped in). The catalyst may be used repeatedly so that the overall consumption of catalyst, relative to the total amount of formose reduced, is considerably lower than in known procedures.

In another variation of the process according to the present invention, the catalyst may be initially introduced into the reactor as a suspension in water or in one of the alcohols described above as suitable solvents. The desired hydrogenation temperature and pressure should then be established and the catalyst activated by prehydrogenation. The formose to be hydrogenated in the form of a solution may then be pumped continuously into the reactor until the reactor is full. The amount of catalyst initially introduced into the hydrogenation reactor should be 4 to 240% by weight, preferably 6 to 100% by weight and most preferably 8 to 35% by weight (based on 100% formose). After pumping in the formose, the mixture should subsequently be hydrogenated for a period corresponding to 3 to 100% of the pumping time. The entire contents should then be forced out of the hydrogenation reactor. The hydrogenated material may then be separated from the catalyst. The recovered catalyst may be used repeatedly.

In another embodiment of the present invention, the formose containing lead and/or calcium as a solution with the suspended catalyst may be pumped continuously through a tube reactor in which the required reaction temperature and pressure have been established. The suspended catalyst should be used in an amount of 4 to 240% by weight, preferably 6 to 100% by weight and most preferably 8 to 35% by weight (relative to the formose content in the formose solution employed). If appropriate, the entire reaction mixture may be pumped in circulation with part of the reaction mixture being removed as the product is formed. The residence time of the formose solution may be determined by the amount of mixture removed relative to the amount of circulating mixture. The mixture removed from the reactor may then be separated into the hydrogenated material and the catalyst. The removed catalyst may be used repeatedly.

It is surprising that "crude formoses" containing the entire catalyst salt content of lead ions and/or calcium ions may be employed in the process according to the present invention, because the prior art teaches that such salt contents deactivate the hydrogenation catalyst within a very short time. This is true especially of the lead ions which are known to be a catalyst poison. It is also surprising that colorless polyol mixtures which require no further purification can be obtained from such formoses by the process of the present invention. It is further surprising that the catalysts employed in the process of the present invention retain their activity despite repeated use. This reusability of the catalysts may be observed not only in the hydrogenation of formoses with a customary catalyst salt content originating from the formose preparation, but also in the case of formoses to which additional amounts of lead ions or of calcium ions were added.

A particularly surprising characteristic of the present invention is the fact that not only does the catalyst retain its hydrogenating activity in the presence of the salt content described, but it also decreases the salt content in the solution to be hydrogenated. For example, the lead ion concentration of a standard formose solution may be reduced to less than 1 ppm, so that virtually lead-free formitol is obtained. In like manner, the calcium ion concentration of a formose solution may be reduced to less than 50%, preferably less than 30%, of the original calcium ion content.

While not wishing to be bound by any theory, it is believed that the decrease in lead ion concentration achieved in the present invention is due to an alloying of zero-valent lead with the catalyst metal. This alloying of the lead (a known catalyst poison) does not prevent re-use of the catalyst provided the lead content of the catalyst does not exceed 30% by weight, preferably 20% by weight (relative to the original weight of the catalyst).

The calcium ion content in the formose to be hydrogenated is decreased during the hydrogenation operation by precipitation as calcium carbonate. It is believed that the formate ions present in the reaction mixture decompose to carbon dioxide, which then converts the calcium ions into substantially insoluble calcium carbonate. At least some of this calcium carbonate precipitates on the catalyst in the form of loosely attached agglomerates. The hydrogenation catalyst retains its catalytic activity relative to the weight of the active metal, however, there is a drop in the specific activity (relative to the toal mass of solid) of the catalyst/calcium carbonate solid. When this catalyst charged with the calcium carbonate precipitate is used repeatedly, an ever larger mass of solid (with the same metal content) is circulated as a suspension in the hydrogenation mixture. For technological and economic reasons, it is therefore appropriate to use such a catalyst only until its precipitated calcium carbonate content does not exceed 100% by weight, preferably 70% by weight and most preferably 40% by weight, of calcium carbonate (relative to the original weight of the catalyst).

The calcium carbonate precipitate may be easily removed from the catalyst, however, because it is only weakly bonded mechanically to the hydrogenation catalyst. In one such procedure, the catalyst coated with calcium carbonate is stirred so vigorously as a suspension in water or another liquid medium which does not dissolve the calcium carbonate (preferably in water), that the loosely adhering calcium carbonate particles become separated from the catalyst particles. In a subsequent quieting phase (achieved, for example, by switching off the stirrer), the catalyst particles settle rapidly to the bottom of the vessel due to their higher density. The calcium carbonate still in suspension may then be decanted off. The catalyst freed in this manner from the calcium carbonate precipitate exhibits no loss in catalytic activity and may be used repeatedly in the process according to the present invention.

The process according to the present invention is particularly advantageous because:

1. "Crude formose", which contains the entire catalyst salt ballast of lead ions and/or calcium ions may be used to make a colorless mixture of low molecular weight polyhydric alcohols without decreasing the lead and/or calcium ion concentration.
2. The amount of catalyst consumed is very low because its activity is maintained thereby allowing repeated use of the catalyst, in spite of the conversion products of the lead ions and/or calcium ions.
3. Formitols which are free from lead and have a low content of calcium ions may be obtained. These formitols, without further purification, are useful for many applications.
4. The hydrogenation proceeds more rapidly than the hydrogenation in prior art processes, particularly when the formose is hydrogenated by a continuous process.
5. Low molecular weight polyalcohols are obtained by splitting long-chain formose constituents (German Offenlegungsschrift No. 2,756,274). A measure of the extent of such splitting is the average OH functionality in the hydrogenated material. Each C atom of the resulting polyalcohols generally carries one OH group.
6. The resulting polyol mixture is colorless. Those polyol mixtures which may be obtained by including additional aldehydes, ketones or polyols in the formose (especially higher-molecular polyols), have an improved compatibility with blowing agents used in the polyisocyanate polyaddition process.

The polyol mixtures (formitols) which may be prepared according to the present invention may be used in many ways. They may be employed directly as polyol chain-lengtheners and/or crosslinking agents in the preparation of polyurethane plastics. They may also be used as starting materials for the preparation of polyethers or polyesters, which in turn can be used for the preparation of polyurethane plastics and other plastics (for example, alkyd resins). These formitols may also be used as antifreezing agents or as formulation auxiliaries in the field of plant protection. p It is also possible to obtain polyether-polyols which have a high number of functional groups by base-catalyzed or acid-catalyzed propoxylation and/or ethoxylation of the polyols of the present invention. In high OH number ranges, these polyether-polyols may be used for the production of rigid or semi-rigid cellular polyurethane plastics. At low OH numbers, the polyether polyols are useful as starting materials for highly elastic polyurethane foams.

Highly branched polyesters which can be synthesized by reacting the polyol mixtures of the present invention with polyhydric carboxylic acids in accordance with known polyester condensation processes (see, e.g., Houben-Weyl, Methoden der Organischen Chemie, Vol. XIV, page 40). Suitable carboxylic acids are phthalic acid, isophthalic acid, terephthalic acid, tetra- and hexahydrophthalic acid, adipic acid or maleic acid.

Inclusion of such highly branched polyesters in alkyd resins improves the hardness of these resins. Such polyesters containing hydroxyl groups may also be used as starting components for the preparation of polyurethane plastics.

The polyhydric alcohols prepared according to the present invention may also be reacted with long-chain, aliphatic monocarboxylic acids to produce esters containing hydroxyl groups. Acids suitable for this reaction include: caprylic acid, capric acid, lauric acid, myristic acid, palmitic acid, stearic acid, oleic acid, linoleic acid, arachidonic acid or behenic acid and derivatives thereof (for example, the methyl or ethyl esters and their anhydrides or mixed anhydrides). These esters, like the oxyethylation products of the polyols and the corresponding carbamic acid esters (K. Lindner, Tenside (Surface-Active Agents) Vol. III, Wissenschaftliche Verlagsgesellschaft Stuttgart, 1964, page 2336), are non-ionic, surface-active compounds which may be used as emulsifiers, wetting agents or plasticizers.

The polyol mixtures produced according to the present invention may also be used as moisture-retention agents in cosmetics and plastics.

The mixtures of polyhydric, low-molecular alcohols of the present invention are, however, preferably used as the polyol component in the polyisocyanate polyaddition process.

Thus, the present invention also relates to a process for the preparation of polyurethane plastics by reaction of (a) a polyisocyanate with a (b) compound which has at least two active hydrogen atoms and has a molecular weight of between 62 and 400 and if appropriate (c) a compound which has at least two active hydrogen atoms and has a molecular weight of between 400 and 10,000. Blowing agents, catalysts and other additives which are known to those in the art may also be included. Mixtures of low-molecular, polyhydric alcohols prepared according to the present invention are employed as component (b) or a portion thereof.

Polyisocyanates which may be used in the preparation of polyurethane plastics in accordance with the abovedescribed process are: aliphatic, cycloaliphatic, araliphatic, aromatic and heterocyclic polyisocyanates such as those described by W. Siefken in Justus Liebigs Annalen der Chemie, 562, pages 75 to 136, corresponding to the formula

Q(NCO)$_n$ in which n = a number from 2 to 4, preferably 2, and

Q denotes an aliphatic hydrocarbon radical with 2-18 (preferably 6-10) C atoms; a cycloaliphatic hydrocarbon radical with 4-15 (preferably 5-10) C atoms; an aromatic hydrocarbon radical with 6-15 (preferably 6-13) C atoms; or an araliphatic hydrocarbon radical with 8-15 (preferably 8-13) C atoms.

Such compounds include: ethylene diisocyanate, tetramethylene 1,4-diisocyanate, hexamethylene 1,6-diisocyanate, dodecane 1,12-diisocyanate, cyclobutane 1,3-diisocyanate, cyclohexane 1,3- and 1,4-diisocyanate and any mixtures of these isomers, 1-isocyanato-3,3,5-trimethyl-5-isocyanatomethylcyclohexane (German Auslegeschrift No. 1,202,785 and U.S. Pat. No. 3,401,190), hexahydrotoluylene 2,4- and 2,6-diisocyanate and any mixtures of these isomers, hexahydrophenylene 1,3- and/or 1,4-diisocyanate, perhydrodiphenylmethane 2,4'- and/or 4,4'-diisocyanate, phenylene 1,3- and 1,4-diisocyanate, toluylene 2,4- and 2,6-diisocyanate and any mixtures of these isomers, diphenylmethane, 2,4'- and/or 4,4'-diisocyanate and naphthylene 1,5-diisocyanate.

Examples of other isocyanates which may be used in the process of the present invention are: triphenylmethane 4,4',4''-triisocyanate, polyphenyl/polymethylene polyisocyanates [such as are obtained by aniline/formaldehyde condensation and subsequent phosgenation (British Pat. Nos. 874,430 and 848,671)], m- and p-isocyanato-phenylsulfonyl isocyanate (U.S. Pat. No. 3,454,606), perchlorinated aryl polyisocyanates (U.S. Pat. No. 3,277,138), polyisocyanates containing carbodiimide groups (U.S. Pat. No. 3,152,162), norbornane diisocyanates (U.S. Pat. No. 3,492,330), polyisocyanates containing allophanate groups (British Pat. No. 994,890), polyisocyanates containing isocyanurate groups (U.S. Pat. No. 3,001,973), polyisocyanates containing urethane groups (U.S. Pat. No. 3,394,164 and U.S. Pat. No. 3,644,457), polyisocyanates containing acylated urea groups (German Pat. No. 1,230,778), polyisocyanates containing biuret groups (U.S. Pat. No. 3,124,605, U.S. Pat. No. 3,201,372 and U.S. Pat. No. 3,124,605), polyisocyanates prepared by telomerization reactions (U.S. Pat. No. 3,654,106), polyisocyanates containing ester groups (U.S. Pat. No. 3,567,763), reaction products of the above-mentioned isocyanates with acetals (German Pat. No. 1,072,385) and polyisocyanates containing polymeric fatty acid esters (U.S. Pat. No. 3,455,883).

It is also possible to employ the distillation residues which are obtained in the industrial manufacture of isocyanate and contain isocyanate groups. These residues may be dissolved in one or more mixtures of the above-mentioned polyisocyanates. Any mixtures of the above-mentioned polyisocyanates can also be used.

Generally, preferred polyisocyanates are those which are commercially available, such as, toluylene 2,4- and 2,6-diisocyanate and any mixtures of these isomers ("TDI"), polyphenyl/polymethylene polyisocyanates (such as are prepared by aniline/formaldehyde condensation and subsequent phosgenation ("crude MDI")) and polyisocyanates containing carbodiimide groups, urethane groups, allophanate groups, isocyanurate groups, urea groups or biuret groups ("modified polyisocyanates"), in particular, modified polyisocyanates which are derived from toluylene 2,4- and/or 2,6-diisocyanate or from diphenylmethane 4,4'- and/or 2,4'-diisocyanate.

In the process for making a polyurethane according to the present invention, a compound with at least two hydrogen atoms, which is reactive towards isocyanates, and having a molecular weight of 62 to 400 is employed. Such compounds, which serve as chain-lengthening agents or crosslinking agents, may contain hydroxyl groups and/or amino groups and/or thiol groups and/or carboxyl groups (preferably hydroxyl groups and/or amino groups). These compounds, as a rule, have 2 to 8, preferably 2 to 4, hydrogen atoms which are reactive towards isocyanates.

It is also possible to use mixtures of various compounds with at least two hydrogen atoms which are reactive towards isocyanates and with a molecular weight of 62 to 400. Examples of such compounds are: ethylene glycol, propylene 1,2- and 1,3-glycol, butylene 1,4- and 2,3-glycol, 1,5-pentanediol, 1,6-hexanediol, 1,8-octanediol, neopentylglycol, 1,4-bis-hydroxymethylcyclohexane, 2-methyl-1,3-propanediol, dibromobutenediol (U.S. Pat. No. 3,723,392), glycerol, trimethylolpropane, hexane-1,2,6-triol, trimethylolethane, pentaerythritol, quinitol, mannitol and sorbitol, castor oil, diethylene glycol, triethylene glycol, tetraethylene glycol, higher polyethylene glycols with a molecular weight of up to 400, dipropylene glycol, higher polypropylene glycols with a molecular weight of up to 400, dibutylene glycol, higher polybutylene glycols with a molecular weight of up to 400, 4,4'-dihydroxydiphenylpropane, dihydroxymethylhydroquinone, ethanolamine, diethanolamine, N-methyldiethanolamine, triethanolamine and 3-aminopropanol.

Other possible low-molecular polyols are mixtures of hydroxyaldehydes, hydroxyketones and polyhydroxy compounds ("formoses") such as are formed when formaldehyde undergoes self-condensation (German Offenlegungsschrift No. 2,639,084). In order to obtain plastics with an improved flame-repellancy, these formoses are advantageously employed in combination with aminoplast-forming agents and/or phosphites (German Offenlegungsschrift No. 2,738,513 and German Offenlegungsschrift No. 2,738,532).

Solutions of polyisocyanate polyaddition products (e.g., polyurethane-ureas containing ionic groups and/or of polyhydrazodicarboxamides) in low-molecular polyhydric alcohols may also be used according to the invention as the polyol component (German Offenlegungsschrift No. 2,638,759).

Component (b) may also be an aliphatic diamine, such as, ethylene diamine, 1,4-tetramethylenediamine, 1,11-undecamethylenediamine, 1,12-dodecamethylenediamine and mixtures thereof, 1-amino-3,3,5-trimethyl-5-aminomethylcyclohexane ("isophoronediamine"), 2,4- and 2,6-hexahydrotoluylenediamine and mixtures thereof, perhydro-2,4'- and 4,4'-diaminodiphenylmethane, p-xylylenediamine, bis-(3-aminopropyl)-methylamine, diaminoperhydroanthracenes (German Offenlegungsschrift No. 2,638,731) and cycloaliphatic triamines (German Offenlegungsschrift No. 2,614,244). Additional compounds which may be used as component (b) are hydrazine; substituted hydrazines, such as methylhydrazine, N,N'-dimethylhydrazine and homologs thereof; acid dihydrazides, for example, carbodihydrazide, oxalic acid dihydrazide, the dihydrazides of malonic acid, succinic acid, glutaric acid, adipic acid, β-methyladipic acid, sebacic acid, hydracrylic acid and terephthalic acid; semicarbazidoalkylene-hydrazides, such as, for example, β-semicarbazidopropionic acid hydrazide (German Offenlegungsschrift No. 1,770,591); semicarbazidoalkylene carbazinates, such as, for example, 2-semicarbazidoethyl carbazinate (German Offenlegungsschrift No. 1,918,504); and amino-semicarbazide compounds, such as β-aminoethyl semicarbazido-carbonate (German Offenlegungsschrift No. 1,902,931). All or some of the amino groups may be blocked by aldimine groups or ketimine groups in order to control their reactivity (U.S. Pat. No. 3,734,894 and German Offenlegungsschrift No. 2,637,115).

Aromatic diamines which may be used as component (b) in making a polyurethane include: bisanthranilic acid esters (German Offenlegungsschrift No. 2,040,644 and German Offenlegungsschrift No. 2,160,590), 3,5- and 2,4-diaminobenzoic acid esters (German Offenlegungsschrift No. 2,025,900), diamines which contain ester groups (described in German Offenlegungsschrift No. 1,803,635, German Offenlegungsschrift No. 2,040,650 and German Offenlegungsschrift No. 2,160,589), diamines containing ether groups (German Offenlegungsschrift No. 1,770,525 and German Offenlegungsschrift No. 1,809,172) 2-halogeno-1,3-phenylenediamines which are optionally substituted in the 5-position (German Offenlegungsschrift No. 2,001,772, German Offenlegungsschrift No. 2,025,896 and German Offenlegungsschrift No. 2,065,869), 3,3'-dichloro-4,4'-diaminodiphenylmethane, toluylenediamine, 4,4'-diaminodiphenylmethane, 4,4'-diaminodiphenyl disulfides (German Offenlegungsschrift No. 2,404,976), diaminodiphenyl dithioethers (German Offenlegungsschrift No. 2,509,404), aromatic diamines substituted by alkylthio groups (German Offenlegungsschrift No. 2,638,760), diaminobenzene phosphonic acid esters (German Offenlegungsschrift No. 2,459,491), aromatic diamines containing sulfonate groups or carboxylate groups (German Offenlegungsschrift No. 2,720,166), and the high-melting diamines described in German Offenlegungsschrift No. 2,635,400. Examples of appropriate aliphatic-aromatic diamines are the aminoalkylthioanilines according to German Offenlegungsschrift No. 2,734,574.

Compounds such as 1-mercapto-3-aminopropane; optionally substituted aminoacids, for example, glycine, alanine, valine, serine and lysine; and optionally substituted dicarboxylic acids, for example, succinic acid, adipic acid, phthalic acid, 4-hydroxyphthalic acid and 4-aminophthalic acid, may also be used as chain-lengthening agents (i.e., compound b)) in the present invention.

Compounds which are monofunctional with respect to isocyanates may be used in amounts of 0.01 to 10% by weight (relative to the polyurethane solid) as chain stoppers. Examples of monofunctional compounds of this type are monoamines, such as butylamine and dibutylamine, octylamine, stearylamine, N-methylstearylamine, pyrrolidine, piperidine and cyclohexylamine; monoalcohols such as butanol, 2-ethylhexanol, octanol, dodecanol; the various amyl alcohols; cyclohexanol and ethylene glycol monoethyl ether.

Other low-molecular weight polyols which have a molecular weight of up to 400 that may be used as component (b) in making a polyurethane in accordance with the present invention are ester-diols such as δ-hydroxybutyl-ε-hydroxycaproic acid esters, ω-hydroxyhexyl-γ-hydroxybutyric acid esters, adipic acid bis-(β-hydroxyethyl)-ester and terephthalic acid bis-(β-hydroxyethyl)-ester; diolurethanes, such as 1,6-hexamethylene-bis-(β-hydroxyethylurethane) or 4,4'-diphenylmethane-bis-(δ-hydroxybutylurethane); and diol-ureas, such as 4,4'-diphenylmethane-bis-(β-hydroxyethylurea), or the compound

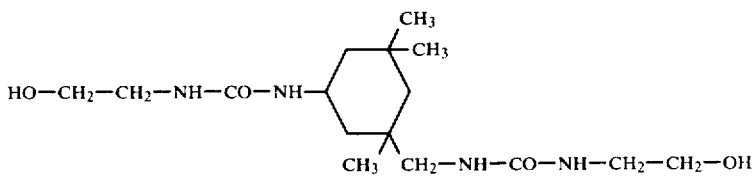

It may be advantageous to employ polyols which contain sulfonate groups and/or phosphonate groups (German Offenlegungsschrift No. 2,719,372), preferably the adduct of bisulfite and 1,4-butanediol, or alkoxylation products thereof.

Mixtures of low-molecular, polyhydric alcohols which may be obtained by reducing the mixtures of low-molecular hydroxyaldehydes, hydroxyketones and polyols obtainable by formaldehyde condensation may be used in the present invention, as all or some of component (b). When these reduced mixtures ("formitols") are used as all or some of component (b), they are used in an amount which may be from 0.1 to 100% by weight, preferably 2-95% and most preferably 10-80% by weight, of the total amount of component (b).

A preferred formitol is that which is obtained, according to the invention, by catalytic reduction of a mixture of low-molecular weight hydroxyaldehydes, hydroxyketones and polyols with hydrogen at 80° to 200° C. and under 100 to 200 bars pressure in the presence of up to 16,000 ppm of lead ions and/or up to 50,000 ppm of calcium ions, and if appropriate, in the presence of other ions of Main Groups IA and/or IIA of the Periodic Table.

Compounds with at least two hydrogen atoms which are reactive toward isocyanates and with a molecular weight of 400-10,000 may be used as component (c) for the preparation, according to the invention, of polyurethane plastics. Suitable compounds may contain amino groups; thiol groups; carboxyl groups; compounds containing hydroxyl groups, in particular, compounds containing two to eight hydroxyl groups and especially those with a molecular weight of 600 to 8,000 (preferably 800 to 4,000) such as polyesters, polyethers, polythioethers, polyacetals, polycarbonates, polyester-amides and polyamides which contain at least two, as a rule 2 to 8 (preferably 2 to 4), hydroxyl groups and others known to those in the art to be suitable for the preparation of homogeneous polyurethanes and cellular polyurethanes.

The possible polyesters containing hydroxyl groups include the reaction products of polyhydric (preferably dihydric and, if appropriate, also trihydric) alcohols with polybasic (preferably dibasic) carboxylic acids. Instead of the free polycarboxylic acids, it would also be possible to use the corresponding polycarboxylic acid anhydrides, corresponding polycarboxylic acid esters of lower alcohols, and mixtures thereof for the preparation of the polyesters. The polycarboxylic acids may be aliphatic, cycloaliphatic, aromatic and/or heterocyclic in nature and can optionally be substituted (for example, by halogen atoms) and/or unsaturated.

The polyethers which may be used according to the present invention and which contain at least two, as a rule two to eight and preferably two to four, hydroxyl groups are also known to those in the art. Such polyethers may be prepared, for example, by self-polymerization of epoxides, such as ethylene oxide, propylene oxide, butylene oxide, tetrahydrofurane, styrene oxide or epichlorohydrin. Such self-polymerization may be carried out in the presence of Lewis catalysts, such as $BF_3$. Polyethers may also be produced by the addition of these epoxides (preferably of ethylene oxide and propylene oxide) to starting components with reactive hydrogen atoms, such as water, alcohols, ammonia or amines. Examples of suitable alcohols are ethylene glycol, propylene 1,3- or 1,2-glycol, trimethylolpropane, glycerol, sorbitol, 4,4'-dihydroxy-diphenylpropane. Suitable amines are aniline, ethanolamine or ethylenediamine. Sucrose-polyethers (German Auslegeschrift No. 1,176,358 and German Auslegeschrift No. 1,064,938) and polyethers started from formitol or formose (German Offenlegungsschrift No. 2,639,083 and German Offenlegungsschrift No. 2,737,951) can also be used as component (c) in making a polyurethane according to the present invention. Polyethers which contain predominantly primary OH groups (up to 90% by weight, relative to all the OH groups present in the polyether) are in many cases preferred material. Polybutadienes containing OH groups are also suitable to the invention.

Polythioethers which may be used as component (c) in making a polyurethane in accordance with the present invention include the condensation products of thiodiglycol with itself and/or with other glycols, dicarboxylic acids, formaldehyde, aminocarboxylic acids or aminoalcohols.

Possible polyacetals are, for example, the compounds which may be prepared from glycols, such as diethylene glycol, triethylene glycol, 4,4'-dihydroxyethoxydiphenyldimethylmethane or hexanediol, and formaldehyde. Polyacetals which are suitable to the present invention may also be prepared by polymerization of cyclic acetals, such as, trioxane (German Offenlegungsschrift No. 1,694,128).

Polycarbonates containing hydroxyl groups suitable to the present invention are known to those skilled in the art. Such polycarbonates may be prepared by reacting diols, such as 1,3-propanediol, 1,4-butanediol and/or 1,6-hexanediol, diethylene glycol, triethylene glycol, tetraethylene glycol or thiodiglycol with diaryl carbonates (for example, diphenyl carbonate) or phosgene (German Auslegeschrift No. 1,694,080, German Auslegeschrift No. 1,915,908 and German Auslegeschrift No. 2,221,751 and German Offenlegungsschrift No. 2,605,024).

The polyester-amides and polyamides which may be used in the present invention include the condensates (which are predominantly linear) obtained from polybasic saturated or unsaturated carboxylic acids or anhydrides thereof and polyfunctional saturated or unsaturated aminoalcohols, diamines, polyamines and mixtures thereof.

It is also possible to use polyhydroxy compounds which already contain urethane groups or urea groups, optionally modified naturally occurring polyols (such as castor oil) or carbohydrates (for example, starch). Products obtained by adding alkylene oxides onto phenol/formaldehyde resins or onto urea/formaldehyde resins may also be employed according to the invention. Such compounds are described in High Polymers, Vol. XVI, "Polyurethanes, Chemistry and Technology", written by Saunders-Frisch, Interscience Publishers, New York, London, Vol. I, 1962, pages 32–42 and pages 44–54 and Vol. II, 1964, pages 5–6 and 198–199, and in Kunststoff-Handbuch (Plastics Handbook), Vol. VII, Vieweg-Höchtlen, Carl-Hanser-Verlag, Munich, 1966, (for example, pages 45–71). Mixtures of the above-mentioned compounds with at least two hydrogen atoms which are reactive toward isocyanates and with a molecular weight of 400–10,000 (for example, mixtures of polyethers and polyesters) may also be employed.

It is also possible to employ blowing agents, catalysts, surface-active additives and reaction retarders as component (d) for the preparation of polyurethane plastics according to the present invention. Examples of blowing agents which may be used are water and/or highly volatile inorganic or organic substances. Suitable organic blowing agents include: acetone; ethyl acetate; halogen-substituted alkanes, such as methylene chloride, chloroform, ethylidene chloride, vinylidene chloride, monofluorotrichloromethane, chlorodifluoromethane and dichlorofluoromethane; and butane, hexane, heptane or diethyl ether. Possible inorganic blowing agents are air, $CO_2$ and $N_2O$. A blowing action may also be achieved by adding compounds which decompose at temperatures above room temperature and thereby split off a gas such as nitrogen. Examples of such compounds are azo compounds, such as azodicarboxamide or azoisobutyronitrile. Further examples of blowing agents and details regarding the use of blowing agents are given in Kunststoff-Handbuch (Plastics Handbook), Vol. VII, edited by Vieweg and Höchtlen, Carl-Hanser-Verlag, Munich, 1966, on pages 108–109, 453–455 and 507–510.

Catalysts which may be used in the present invention are well known to those in the art. Examples of suitable catalysts are: tertiary amines, such as triethylamine, tributylamine, N-methyl-morpholine, N-ethyl-morpholine, N,N,N',N'-tetramethyl-ethylenediamine, pentamethyl-diethylenetriamine and higher homologs (German Offenlegungsschrift No. 2,624,527 and German Offenlegungsschrift No. 2,624,528), 1,4-diazabicyclo[2,2,2]octane, N-methyl-N'-dimethylaminoethylpiperazine, bis-(dimethylaminoalkyl)-piperazines (German Offenlegungsschrift No. 2,636,787), N,N-dimethylbenzylamine, N,N-dimethylcyclohexylamine, N,N-diethylbenzylamine, bis-(N,N-diethylaminoethyl)adipate, N,N,N',N'-tetramethyl-butane-1,3-diamine, N,N-dimethyl-β-phenylethylamine, 1,2-dimethylimidazole, 2-methylimidazole; monocyclic and bicyclic amidines (German Offenlegungsschrift No. 1,720,633), bis-(dialkylamino)alkyl ethers (U.S. Pat. No. 3,330,782, German Auslegeschrift No. 1,030,558, German Offenlegungsschrift No. 1,804,361 and German Offenlegungsschrift No. 2,618,280); and tertiary amines, containing amide groups (preferably formamide groups), according to German Offenlegungsschrift No. 2,523,633 and German Offenlegungsschrift No. 2,732,292. Mannich bases which are known to those in the art are also possible catalysts. Mannich bases may be obtained from secondary amines (such as dimethylamine) and aldehydes (preferably formaldehyde) or ketones (such as acetone, methyl ethyl ketone or cyclohexanone) and phenols (such as phenol, nonylphenol or bisphenol).

Tertiary amines which contain hydrogen atoms which are active with respect to isocyanate groups and which are effective as a catalyst are triethanolamine, triisopropanolamine, N-methyl-diethanolamine, N-ethyldiethanolamine, N,N-dimethyl-ethanolamine and reaction products thereof with alkylene oxides (such as propylene oxide and/or ethylene oxide) as well as secondary-tertiary amines (German Offenlegungsschrift No. 2,732,292).

Sila-amines with carbon/silicon bonds such as 2,2,4-trimethyl-2-silamorpholine and 1,3-diethylaminomethyl-tetramethyl-disiloxane (described in German Patent Specification No. 1,229,290) are also possible catalysts.

Other catalysts which may be used are nitrogen-containing bases such as tetraalkylammonium hydroxides; alkali metal hydroxides, such as sodium hydroxide; alkali metal phenolates, such as sodium phenolate; and alkali metal alcoholates, such as sodium methylate. Hexahydrotriazines may also be employed as catalysts (German Offenlegungsschrift No. 1,769,043).

The reaction between NCO groups and hydrogen atoms which are active in Zerewitinoff reactions is also greatly accelerated by lactams and azalactams (German Offenlegungsschrift No. 2,062,288, German Offenlegungsschrift No. 2,062,289, German Offenlegungsschrift No. 2,117,576, German Offenlegungsschrift No. 2,129,198, German Offenlegungsschrift No. 2,330,175 and German Offenlegungsschrift No. 2,330,211).

Organic metal compounds, in particular, organic tin compounds, may also be used as catalysts in the process according to the present invention. Suitable organic tin compounds include: di-n-octyl-tin mercaptide (German Auslegeschrift No. 1,769,367 and U.S. Pat. No. 3,645,927); tin-II salts of carboxylic acids, such as tin-II acetate, tin-II octoate, tin-II ethylhexoate and tin-II laurate; and tin-IV compounds for example, dibutyl-tin oxide, dibutyl-tin dichloride, dibutyl-tin diacetate, dibutyl-tin dilaurate, dibutyl-tin maleate and dioctyl-tin diacetate.

All of the above-mentioned catalysts may, of course, also be employed as mixtures. Combinations which are of particular interest are organic metal compounds and amidines, aminopyridines, or hydrazinopyridines (German Offenlegungsschrift No. 2,434,185, German Offenlegungsschrift No. 2,601,082 and German Offenlegungsschrift No. 2,603,834).

Other catalysts which may be used in the present invention and details regarding their mode of action are given in Kunststoff-Handbuch (Plastics Handbook), Vol. VII, edited by Vieweg and Höchtlen, Carl-Hanser-Verlag, Munich, 1966, pages 96–102.

The catalysts are generally employed in an amount of between about 0.001 and 10% by weight, relative to the total amount of compounds with at least two hydrogen atoms which are reactive toward isocyanates.

Suitable surface-active additives are emulsifiers and foam stabilizers. Appropriate emulsifiers include: the sodium salts of castor oil, sulfonic acids or salts of fatty acids and amines, such as diethylamine oleate or diethanolamine stearate. Alkali metal salts of ammonium, of sulfonic acids (such as dodecylbenzenesulfonic acid or dinaphthylmethanedisulfonic acid) of fatty acids, (such as ricinoleic acid) or of polymeric fatty acids may also be used as surface-active additives.

Suitable foam stabilizers are polyether-siloxanes, especially those which are water-soluble. These compounds are generally built up in a manner such that a copolymer of ethylene oxide and propylene oxide is bonded to a polymethylsiloxane radical (U.S. Pat. No. 2,834,748, U.S. Pat. No. 2,917,480 and U.S. Pat. No.

3,629,308). The polysiloxane/polyoxyalkylene copolymers (German Offenlegungsschrift No. 2,558,523) which are branched via allophanate groups are especially useful in many cases.

Examples of other additives which may be used in making a polyurethane in accordance with the present invention are: reaction retarders, such as acid substances (for example, hydrochloric acid) or organic acid halides; cell regulators known to those in the art such as paraffins, fatty alcohols and dimethyl-polysiloxanes; pigments or colorants; flameproofing agents known to those in the art such as tris-chloroethyl phosphate, tricresyl phosphate or ammonium phosphate or polyphosphate; agents which stabilize the product against the effects of ageing and weathering; plasticizers; fungistatically and bacteriostatically active substances; and fillers, such as barium sulfate, kieselguhr, carbon black or whiting.

Further examples of surface-active additives and foam stabilizers as well as cell regulators, reaction retarders, stabilizers, flameproofing substances, plasticizers, colorants, fillers and fungistatically and bacteriostatically active substances which may be used according to the present invention, and details regarding the manner in which these additives are used and their mode of action are given in Kunststoff-Handbuch (Plastics Handbook), Vol. VII, edited by Vieweg and Höchtlen, Carl-Hanser-Verlag, Munich, 1966, on pages 103–113.

In the practice of the present invention, the reactants may be reacted by the one-stage process, the prepolymer process or the semi-prepolymer process. Each of these types of processes is known to those in the art. Mechanical equipment which may be used is described in U.S. Pat. No. 2,764,565. Details regarding suitable processing equipment are given in Kunststoff-Handbuch (Plastics Handbook), Vol. VII, edited by Vieweg and Höchtlen, Carl-Hanser-Verlag, Munich, 1966, pages 121–205.

In the production of foam, according to the present invention, foaming may be carried out in closed molds. The mold may be metal, for example, aluminum, or plastic, for example, epoxide resin. The reaction mixture which is capable of foaming is introduced into a mold where it foams and forms the molded article. Foaming in the mold may be carried out in a manner such that the surface of the molded product has a cellular structure. Foaming may also be carried out in a manner such that the molded product has a compact skin and a cellular core. The reaction mixture which is capable of foaming may be introduced into the mold in an amount such that the foam formed just fills the mold or in an amount which is greater than necessary to fill the inside of the mold with foam. The latter procedure which is known as "over-charging" is described in U.S. Pat. No. 3,178,490 and U.S. Pat. No. 3,182,104.

In the case of foaming in the mold, "external release agents" which are known to those in the art (such as silicone oils) may be used. It is also possible to use so-called "internal release agents", such as those disclosed in German Offenlegungsschrift No. 2,121,670 and German Offenlegungsschrift No. 2,307,589, if appropriately mixed with external release agents.

Cold-curing foams may also be produced according to the invention (see, British Pat. No. 1,162,517 and German Offenlegungsschrift No. 2,153,086).

It is also possible to produce foams by block foaming or by the twin conveyor belt process, both of which are known to those in the art.

Exclusive reaction of polyhydroxy compounds (i.e., without also using other components which are reactive towards isocyanates) with polyisocyanates which are capable or producing an elastic product, such as polyisocyanates with a biuret structure (German Auslegeschrift No. 1,543,178) yields hard coatings and lacquers which are lightfast, scratch-resistant and resistant to solvents.

The polyurethane plastics prepared according to the present invention are characterized by a high tensile strength and good dimensional stability. Having thus described our invention, the following examples are given by way of illustration. Unless otherwise indicated, all percentages in these examples are percents by weight.

EXAMPLES

EXAMPLE 1

(Comparison Example "batch hydrogenation")

44 g of Raney nickel in 400 ml of water were initially introduced into a 3 l autoclave and prehydrogenated at 140° C. and under a H$_2$ pressure of 150 bars for 45 minutes. The mixture was then allowed to cool and 1,845 g (approx. 1.5 l) of formose solution which was 47.8% strength by weight, lead-free and adjusted to a pH of 9.0 with Ca(OH)$_2$ (in accordance with Example 2 II from German Offenlegungsschrift No. 2,721,186) were added. The temperature was increased to 80° C. and hydrogenation was carried out under a hydrogen pressure of 150 bars for 5 hours, with the temperature being increased at a rate of 20° C. per hour until it reached 140° C. The mixture was subsequently hydrogenated for the remaining period at this temperature. The solution was then forced out, filtered and analyzed. The black-brown filtrate had a pH value of 6.2 and colored Fehling's solution red indicating that the filtrate still contained reducing constituents.

This example clearly shows that batch hydrogenation of formose by a process which is used in the reduction of D-glucose to sorbitol does not yield a suitable product of low molecular weight polyhydric alcohols.

EXAMPLE 2

("Charge-wise pump hydrogenation")

400 g of Raney nickel/iron (85/15) in 1.5 l of formitol which had 40% strength by weight and a pH of 9.0 (prepared according to Example 3 of German Offenlegungsschrift No. 2,756,270) were initially introduced into a 3 high-grade steel autoclave, heated to 140° C. under a H$_2$ pressure of 180 bars and prehydrogenated for 30 minutes.

500 ml of formose solution which had a 40% strength by weight, d=1.16, Ca content of 6,783 ppm and Pb content of 26 ppm after precipitation of lead sulfate (prepared according to Example 2 II in German Offenlegungsschrift No. 2,721,186) which had first been adjusted to a pH of 9.3 were then pumped into the autoclave in the course of 20 minutes. Subsequent hydrogenation was then carried out under a H$_2$ pressure of 150 bars and at 140° C. for 20 minutes. 500 ml of solution were forced out via a riser tube with a frit which held back the catalyst. The same procedure was then followed by an additional 500 ml charge of formose solution. The hydrogenated solutions were collected and analyzed. The colorless polyol mixture had a residual content of reducing groups (determined as carbonyl) of 0.004%, a residual content of calcium of 1,900 ppm, a residual content of lead of <1 ppm and an average number of OH groups (calculated from the analysis by gas chromatography) of 4.0. Even after 20 cycles, no deactivation of the catalyst was detected.

EXAMPLES 3 TO 10

("Continuous pump hydrogenation")

General experimental conditions:

The catalyst Raney nickel/iron (85/15) in a little water was initially introduced into the autoclave and activated at 140° C. under a $H_2$ pressure of 150 bars for 45 minutes.

The formose solutions (crude products with a salt ballast) according to Example 1 in German Offenlegungsschrift No. 2,738,512 (for Example 3), according to Example 1 in German Offenlegungsschrift No. 2,721,186 (for Example 8) and according to 2 II in German Offenlegungsschrift No. 2,721,186 (for Examples 4–7, 9 and 10) were adjusted to the desired alkalinity with $Ca(OH)_2$ and the operating amount given for the particular type of autoclave was then pumped continuously into the reactor such that the pressure did not fall below 150 bars and the temperature did not fall below 140° C. The mixture was subsequently hydrogenated for about 1/10 of the pumping time and then forced out. The polyol mixture (formitol), which was colorless after separating off the catalyst, was analyzed and, if appropriate, freed from water in vacuo and from the calcium still present by precipitation with sulfuric acid. The average number of OH groups shown (distribution of the components) was calculated from the analysis by gas chromatography.

A rigid, finely cellular foam with good tensile strength and dimensional stability was obtained.

What is claimed is:

1. A process for preparing a mixture of low-molecular weight polyhydroxyl compounds by catalytically hydrogenating a formose mixture with hydrogen on a metal catalyst at elevated temperature and pressure and at a pH of 7.5 to 12.5 in which
   (a) the formose mixture comprises:
      (i) up to 70 wt. % formose,
      (ii) up to 1.6 wt. % lead ions, and
      (iii) up to 5 wt. % calcium ions
   with at least one of (ii) or (iii) being present; and
   (b) the catalyst which is present in an amount of 4–240 wt. % (based on formose solution) is a compound taken from the group consisting of nickel, cobalt and compounds thereof.

2. The process of claim 1, wherein the formose mixture further comprises ions of a metal taken from the group consisting of Group IA, Group IIA and mixtures thereof.

3. The process of claim 1, wherein the formose mixture further comprises a compound taken from the group consisting of aldehydes, ketones, alcohols, sugars and mixtures thereof, which compound did not originate from preparation of the formose.

4. The process of claim 1, wherein the formose mixture is hydrogenated with a stationary catalyst on a non-continuous basis.

5. The process of claim 1, wherein the catalyst is in the form of a suspension.

6. The process of claim 5, wherein the formose mixture is hydrogenated on a continuous basis.

7. The process of claim 6, wherein the formose mixture is hydrogenated in a reactor for a period of time which is 3 to 100% of the period required to pump enough of the formose mixture to fill the reactor.

| Example Number | Autoclave (1) | Formose (kg) | Concentration (%) | $Ca^{2+}$ [ppm] | $Pb^{2+}$ [ppm] | Catalyst* (g) | pH after adjustment with $Ca(OH)_2$ | Total hydrogenation time [hrs] | Residual Content of Carbonyl (%) | Residual Content of $Ca^{2+}$ [ppm] | Residual Content of $Pb^{2+}$ [ppm] | Avg. No. of OH Groups |
|---|---|---|---|---|---|---|---|---|---|---|---|---|
| 3 | 3 | 1.735 | 48 | 26,210 | — | 133 | 9.0 | 7 | 0.008 | 4,600 | — | 4.9 |
| 4 | 3 | 1.735 | 48 | 10,450 | 431 | 133 | 9.0 | 7 | 0.008 | 3,600 | <1 | 3.9 |
| 5 | 3 | 1.735 | 68.3 | 9,940 | 620 | 133 | 9.1 | 7 | 0.006 | 3,300 | <1 | 3.9 |
| 6 | 3 | 1.735 | 36.6 | 12,100 | 260 | 133 | 9.1 | 1.75 | 0.03 | 1,800 | <1 | 4.2 |
| 7 | 3 | 1.735 | 47.8 | 10,000 | 15,330*** | 133 | 8.6 | 7 | 0.03 | 4,200 | <1 | 4.0 |
| 8 | 3 | 1.735 | 45.5 | —** | 923 | 133 | 9.1** | 7 | 0.004 | — | <1 | 4.1 |
| 9 | 1,800 | 1.042 | 47.8 | 9,770 | — | 80,000 | 9.0 | 7 | 0.04 | 2,250 | — | 4.0 |
| 10 | 1,800 | 966 | 65 | 9,990 | 620 | 80,000 | 9.0 | 7 | 0.006 | 2,000 | <1 | 4.0 |

*In each of these Examples the catalyst was re-used.
**Rendered alkaline with NaOH: total Na content: 5,600 ppm
***Contains subsequently added Pb ions

EXAMPLE 11

Production of a polyurethane foam 25 parts by weight of a polypropylene oxide started on ethylenediamine (OH number: 74), 22 parts by weight of the formitol from Example 9, 10 parts by weight of trichloroethylphosphate, 15 parts by weight of monofluorotrichloromethane, 0.5 part by weight of dimethylbenzylamine, 0.5 part by weight of a commercially available silicone stabilizer (L 5420 from UCC) and 75 parts by weight of an industrial phosgenation product of aniline/formaldehyde condensates (NCO content: 29%) were mixed intensively and the mixture allowed to foam in an open mold.

8. The process of claim 6, wherein the catalyst is separated from the mixture of low-molecular weight polyhydroxyl compounds and reused.

9. The process of claim 1, wherein the catalyst is reused until its lead content exceeds 30 wt. % of the initial weight of the catalyst.

10. The process of claim 1, wherein the catalyst is reused until its content of precipitated calcium carbonate exceeds 100 wt. % of the initial weight of the catalyst.

11. The process of claim 10, wherein the precipitated calcium carbonate is removed from the catalyst by vigorously stirring the catalyst upon which the calcium carbonate is precipitated, allowing the heavy catalyst particles to settle and decanting off the suspended calcium carbonate particles.

* * * * *